(12) United States Patent
Andersen

(10) Patent No.: US 9,801,408 B2
(45) Date of Patent: *Oct. 31, 2017

(54) NICOTINE DELIVERY PRODUCT AND METHOD FOR PRODUCING IT

(71) Applicant: Fertin Pharma A/S, Vejle, Ost (DK)

(72) Inventor: Carsten Andersen, Vejle (DK)

(73) Assignee: FERTIN PHARMA A/S, Vejle Ost (DK)

( * ) Notice: Subject to any disclaimer, the term of this patent is extended or adjusted under 35 U.S.C. 154(b) by 0 days.

This patent is subject to a terminal disclaimer.

(21) Appl. No.: 14/260,932

(22) Filed: Apr. 24, 2014

(65) Prior Publication Data

US 2014/0230833 A1 Aug. 21, 2014

Related U.S. Application Data

(63) Continuation of application No. 10/581,628, filed as application No. PCT/DK2004/000841 on Dec. 2, 2004, now Pat. No. 8,741,935.

(60) Provisional application No. 60/509,063, filed on Dec. 5, 2003.

(30) Foreign Application Priority Data

Dec. 2, 2003 (DK) .................................. 2003 01782

(51) Int. Cl.
| | |
|---|---|
| A24B 15/16 | (2006.01) |
| A01N 37/18 | (2006.01) |
| A24B 15/10 | (2006.01) |
| A61K 9/68 | (2006.01) |
| A61K 31/465 | (2006.01) |
| A61K 47/10 | (2017.01) |
| A61K 47/48 | (2006.01) |
| A24B 15/28 | (2006.01) |

(52) U.S. Cl.
CPC ............ *A24B 15/10* (2013.01); *A24B 15/287* (2013.01); *A61K 9/0058* (2013.01); *A61K 31/465* (2013.01); *A61K 47/10* (2013.01); *A61K 47/48184* (2013.01)

(58) Field of Classification Search
CPC ................................ A24B 15/16; A01N 33/18
See application file for complete search history.

(56) References Cited

U.S. PATENT DOCUMENTS

| | | | |
|---|---|---|---|
| 3,845,217 A | 10/1974 | Ferno et al. | |
| 3,901,248 A | 8/1975 | Lichtneckert et al. | |
| 4,692,462 A | 9/1987 | Banerjee | |
| 5,935,604 A | 8/1999 | Illum | |
| 6,586,449 B1 | 7/2003 | Walling | |
| 2002/0015687 A1 | 2/2002 | Bellamy | |

FOREIGN PATENT DOCUMENTS

| | | |
|---|---|---|
| WO | WO 94/08572 | 4/1994 |
| WO | WO 03/061709 | 7/2003 |

OTHER PUBLICATIONS

United States Pharmacopeial Convention, Inc., The United States Pharmacopeia, The National Formulary, Jan. 1, 2002, vol. 25, pp. 1225-1226.
United States Pharmacopeial Convention, Inc., The United States Pharmacopeia, The National Formulary, Jan. 1, 2002, vol. 26, pp. 1309-1310.

*Primary Examiner* — Tracy Liu
(74) *Attorney, Agent, or Firm* — Merchant & Gould P.C.

(57) ABSTRACT

A nicotine delivery product comprising the reaction product of a nicotine/cation exchange resin complex and an organic polyol; and a method for preparing it comprising (a) mixing an aqueous suspension of a nicotine/cation exchange resin complex with an organic polyol or an aqueous solution thereof, and (b) removing water from the mixture to produce said nicotine delivery product. The nicotine delivery product has a nicotine release rate of at least 80% over a 10 minute period. It is particularly suited for use in smoking substitution devices delivering nicotine such as chewing gum, patches, lozenges, melting tablets and tablets for chewing.

18 Claims, No Drawings

NICOTINE DELIVERY PRODUCT AND METHOD FOR PRODUCING IT

This application is a Continuation Application of U.S. Ser. No. 10/581,628, filed 16 Mar. 2007, which is a National Stage Application of PCT/DK2004/000841, filed 2 Dec. 2004, which claims benefit of U.S. Provisional Ser. No. 60/509,063, filed 5 Dec. 2003, and which claims benefit of PA200301782, filed 2 Dec. 2003 in Denmark, and which applications are incorporated herein by reference. To the extent appropriate, a claim of priority is made to each of the above disclosed applications.

FIELD OF THE INVENTION

This invention relates to a nicotine delivery product comprising nicotine, a cation exchange resin and a polyol, such product having a nicotine release rate of at least 80% over a 10 minute period, as well as a method for producing it.

BACKGROUND OF THE INVENTION

Nicotine is a well known, highly characterized alkaloid that can be isolated from the dried leaves of *Nicotiana tabacum*. Its numerous commercial uses include utilities such as a fumigant, an insecticide and the like. It is of therapeutically valuable in the treatment of the smoking withdrawal syndrome. This treatment is based on the fact that the administration of nicotine into the body has been readily accomplished by the method of smoking, e.g., from cigarettes, pipes or cigars. The smoker experiences a satisfactory sensation from such administration. However, smoking may be associated with health hazards not necessarily associated with administration of nicotine itself.

As a result, non-smoking methods have been devised to administer nicotine to the body. These include nicotine containing chewing gums, nicotine-impregnated dermal patches, nicotine inhalers and the like. A variety of patents have disclosed such products.

U.S. Pat. No. 4,692,462 discloses a transdermal drug delivery system having a drug reservoir composed, in part, of an ion exchange resin. The drug reservoir also contains water and a hydrophilic polymer gel. The presence of the water causes the drug to become unbound and therefore to have a disadvantageously short shelf life.

WO 94/08572 is similar to the above-identified U.S. Pat. No. 4,692,462 but has a non-aqueous component, which increases the shelf life. U.S. Pat. No. 3,901,248 discloses a chewable smoking substitute composition which comprises a chewing gum base and a nicotine/cation exchange resin complex dispersed in said gum base. When such composition is chewed, nicotine is released in small and reduced amounts into the mouth, within the first few minutes of chewing. The composition is marginally effective in inducing the pleasurable sensation of smoking that is typically desired from those engaged in the therapy that incorporates such chewing gum. There is no disclosure of a polyol in intimate contact with a nicotine/cation exchange resin complex.

U.S. Pat. No. 6,586,449 discloses in claim 1 a method for preparing a nicotine composition having a nicotine release rate of not less than 70% over a 10 minute period said method comprising (a) mixing an aqueous solution of an organic polyol with a cation exchange resin selected from the group consisting of (i)—a methacrylic, weakly acidic type of resin containing carboxylic functional groups, (ii)—a polystyrene, strongly acidic type of resin containing sulfonic functional groups, and (iii)—a polystyrene, intermediate acidic type of resin containing phosphoric functional groups, thereby forming a cation exchange resin mixture having some of its ion exchange sites partially blocked with said polyol; (b) admixing with said mixture of step (a) an aqueous solution of nicotine to form a nicotine-coated cation exchange resin admixture; and (c) removing water from said admixture to produce said nicotine composition having a nicotine release rate of not less than 70% over a 10 minute period.

It is explained in the patent specification that in carrying out the claimed process it is necessary to combine the organic polyol with the cation exchange resin to form a mixture (slurry). Thereby, as stated in claim 1 above, a cation exchange resin mixture is formed having some of its ion exchange sites partially blocked with said polyol. To the mixture thus formed is admixed an aqueous solution of nicotine, and the admixture is then dried to remove the water. According to the Examples, release rates of nicotine from dried compositions prepared in this way with different polyols were in the range of 70-77%, compared to 65-66% without polyol, over a 10 minute period determined according to the procedure set forth in the U.S.P. Official Monograph, Volume 25, pages 1225 and 1226.

SUMMARY OF THE INVENTION

Surprisingly, we have now found that by reacting a nicotine/cation exchange resin complex of the kind described in U.S. Pat. No. 3,901,248 with an organic polyol in aqueous solution and drying the resulting product, a nicotine delivery product is obtained which has the same nicotine loading capacity as the compositions disclosed in U.S. Pat. No. 3,901,248 and U.S. Pat. No. 6,586,449, but has an even higher nicotine release rate of at least 80% over a 10 minute period.

Accordingly, the present invention provides a nicotine delivery product comprising an intimate mixture of the reaction product of a nicotine/cation exchange resin complex and an organic polyol.

In is broadest aspect the invention relates to an intimate mixture of the reaction product of a nicotine/cation exchange resin complex and an organic polyol.

In addition, the present invention provides a method for preparing a nicotine delivery product said method comprising (a) mixing an aqueous suspension of a nicotine/cation exchange resin complex with an organic polyol or an aqueous solution thereof, and (b) removing water from the mixture to produce said nicotine delivery product.

In another aspect, the present invention provides a method for preparing a nicotine delivery product said method comprising:

(a) mixing an aqueous solution of nicotine with a cation exchange resin thereby forming a nicotine/cation exchange resin complex, (b) admixing with said complex of step (a) in aqueous suspension an organic polyol or an aqueous solution thereof to form an aqueous slurry of nicotine/cation exchange resin complex incorporating organic polyol, and (c) removing water from said slurry to produce said nicotine delivery product.

Generally, nicotine/cation exchange resin complexes suitable for use according to this invention are complexes of nicotine with a cation exchange resin selected from the group consisting of:

(i) a methacrylic, weakly acidic type of resin containing carboxylic functional groups
(ii) a polystyrene, strongly acidic type of resin containing sulfonic functional groups and
(iii) a polystyrene, intermediate acidic type of resin containing phosphonic functional groups.

Generally, organic polyols suitable for use according to this invention are non-toxic C2 to C12 linear or branched hydrocarbons having at least 2 hydroxy groups and non-toxic C5 to C12 cyclic or heterocyclic hydrocarbons having at least 2 hydroxy groups.

Further, the present invention relates to a chewable gum composition comprising a chewing gum base and a nicotine delivery product as defined above substantially uniformly distributed in said chewing gum base.

DETAILED DESCRIPTION OF THE INVENTION

In accordance with the present invention, a nicotine delivery product, methods for preparing such nicotine delivery product, and compositions containing such nicotine delivery product are provided. The nicotine in the nicotine delivery product herein has a release rate of not less than 80% over a period of 10 minutes. The method by which such release rate is determined is described in more detail in the U.S. P. Official Monograph, Volume 26, pages 1309-1310.

The product produced by the process according to the present invention contains, in addition to the above disclosed nicotine, a cation exchange resin and an organic polyol.

The higher release rate for products according to the present invention is surprising and, without being bound by any theory, we may offer the following explanation:

In a product without polyol, the binding between nicotine and the cationic resin is dominated by ionic bonds.

The same type of binding is found in the product according to the present invention, but is expected to be covered by the added polyol giving a high concentration of polyol on the surface of the particles.

In the process disclosed in U.S. Pat. No. 6,586,449 a fraction of the ionic binding sites are physically blocked by the polyol which will also penetrate deeper into the resin particles before the loading of nicotine. The particles will therefore have a relatively high concentration of polyol in the center with nicotine on the surface.

In the release test according to the U.S.P. monograph the product is treated with a solution containing sodium chloride ions, which will start an ion exchange reaction with the nicotine resin complex resulting in the release of the ionically bound nicotine.

It is believed that the polyol will act as an humectant during the release test and thus give rise to a better contact between the resin complex and the test solution. This effect will be more pronounced in the product according to the present invention due to the very high concentration of polyol on the surface of the resin complex particles, which may explain the observed difference in release rates.

Any non-ionic pharmaceutical grade cationic ion exchange resin used to bind anionic molecules at the ion exchange sites may be employed in this invention. Examples of such cationic materials are: those bearing a carboxylic acid group, such as a weakly acidic type of resins containing carboxylic functional groups (these resins are typically derived from polymers or copolymers of methacrylic acid or polymethacrylic acid); the strongly acidic type of resins containing sulfonic functional groups (these resins are typically derived from polymers of styrene or copolymers of styrene and divinylbenzene); or the intermediate acidic type of resins containing phosphonic acid functional groups (these resins are typically derived from polymers of styrene or copolymers of styrene and divinylbenzene).

Cationic ion exchange resins are well known in the art and the present invention encompasses all of these. Representative cation exchange resins of use in accordance with the present invention are disclosed in U.S. Pat. No. 3,901,248. The preferred cation exchange resins are those known in the art as the Amberlite® resins and include, for example, Amberlite® IR20, Amberlite® IRP69, Amberlite® IRP64, Amberlite® IRP58, Amberlite® IRC50, Amberlite® IRP69, etc.

The product in accordance with the present invention also contains an organic polyol. The organic polyol is a non-toxic C2 to C-12 linear or branched hydrocarbon having at least 2 hydroxy groups or a non-toxic C5 to C-12 cyclic or heterocyclic hydrocarbon having at least 2 hydroxy groups.

The presence of a polyol also facilitates improved handling of the nicotine delivery product because it reduces the dust from the material.

Preferably the nicotine delivery product is an intermediate product for used in the manufacture of a final nicotine delivery product such as a chewing gum. The chewing gum additionally can comprise further polyols.

Examples of such polyols are:

C3
1,2 Propanediol (propylene glycol), 1,3 propanediol (trimethylene glycol),
1,2,3 propanetriol (glycerol);
C4
Erythritol;
C5
Xylitol;
C6
Sorbitol, mannitol, 1,6 hexanediol, cyclohexanehexol (inositol);
C12
Maltitol, maltitol syrup, lactitol, isomalt;
Mono- and disaccharides
Glucose, glucose syrup, fructose, sucrose.

In the first step of the process according to the present invention an aqueous solution of nicotine is mixed with the cation exchange resin to form a slurry of nicotine resin complex in water. The ratio of cation exchange resin to nicotine is from about 1:1 to about 10:1, preferably from 2:1 to 6:1, and most preferably about 4:1.

To ensure a fast and complete reaction between nicotine and the cation exchange resin it is important to include a sufficient amount of water in the mixture. The percent of total added water in the process before drying is suitably from 15 to 90% by weight, preferably from 25 to 65% by weight.

In the process according to this invention the organic polyol is adsorbed to the nicotine cation exchange resin complex. The ratio of resin to polyol is from about 1:1 to about 10:1, preferably from 2:1 to 8:1, and most preferably about 2,4:1.

The resulting aqueous slurry of the nicotine/cation exchange resin complex with adsorbed organic polyol is then dried to remove the water. Such drying can be carried out by any conventional means, i.e. dried over a purge of nitrogen, dried under vacuum, etc. However, during the drying procedure temperatures in excess of 75-80° C. should be avoided as this may cause loss of nicotine. Preferably, the temperature should be kept below 60° C.

The dried product is typically milled and/or sieved to a substantially uniform particle size before being used.

The nicotine delivery product according to this invention is particularly suited for use in smoking substitution devices delivering nicotine such as chewing gum, patches, lozenges, melting tablets and tablets for chewing.

The following Examples illustrate the method of the present invention and the nicotine delivery product resulting from such method. These Examples should not be regarded as limiting the invention in any sense.

EXAMPLES

Procedure A

A 40 liter Stephan mixer equipped with scraper and stirrer was charged with 4.32 kg of ion exchange resin Amberlite® IRP64. In a separate container 1.08 kg of nicotine was mixed with 8.75 kg of water for to 1 minute and the solution added to the mixer. The nicotine container was rinsed with further 2 kg of water which was also added to the mixer. The mixer was closed and stirred for 60 minutes.

Then, a mixture of 1.80 kg of glycerol and 1 kg of water was added to the mixer, and the slurry was stirred for 20 minutes.

Thereafter, the slurry was dried by heating to max. 60° C. under vacuum at a pressure of about 30-100 mbar (about 25-75 mmHg) with stirring. The drying process was stopped when the water content was about 3% by weight.

Results

The dried sample was analysed for nicotine content and release rate according to the method specified in the U.S.P. Official Monograph, Volume 26, pages 1309-1310.

| Content of nicotine % by weight | Water content % by weight | Release of nicotine % over 10 min |
| --- | --- | --- |
| 14.9 | 3.4 | 86 |

Procedure B

A 20 liter Diosna laboratory mixer VAC 20 equipped with scraper and stirrer was charged with 5.00 kg of water. 0.60 kg of nicotine was added and the nicotine container was rinsed with further 0.50 kg of water and was also added to the mixer.

The mixer was closed and stirred for 5 minutes.

Then 2.40 kg of ion exchange resin Amberlite® IRP64 was added to the mixer.

Then, a mixture of 1.00 kg of glycerol and 0.5 kg of water was added to the mixer, and the slurry was stirred for 15 minutes.

Thereafter, the slurry was dried by heating to max. 60° C. under vacuum at a pressure of about 30-100 mbar (about 25-75 mmHg) with stirring. The drying process was stopped when the water content was about 3% by weight.

The invention claimed is:

1. A method of preparing a nicotine delivery product, said method comprising:
    (a) mixing an aqueous suspension of a nicotine/cation exchange resin complex with an organic polyol or an aqueous solution thereof, and
    (b) removing water from the mixture to produce said nicotine delivery product having a nicotine release rate of at least 80% over a 10 minute period.

2. A method of preparing a nicotine delivery product, said method comprising:
    (a) mixing an aqueous solution of nicotine with a cation exchange resin thereby forming a nicotine/cation exchange resin complex in aqueous suspension,
    (b) admixing with said complex of step (a) in aqueous suspension an organic polyol or an aqueous solution thereof to form an aqueous slurry of nicotine/cation exchange resin complex incorporating polyol, and
    (c) removing water from said slurry to produce said nicotine delivery product having a nicotine release rate of at least 80% over a 10 minute period.

3. A method according to claim 1, wherein the cation exchange resin is selected from the group consisting of:
    (i) a methacrylic, weakly acidic type of resin containing carboxylic functional groups
    (ii) a polystyrene, strongly acidic type of resin containing sulfonic functional groups, and
    (iii) a polystyrene, intermediate acidic type of resin containing phosphonic functional groups.

4. The method according to claim 3, wherein the cation exchange resin is a methacrylic, weakly acidic type of resin containing carboxylic functional groups.

5. The method according to claim 4, wherein the cation exchange resin is polacrilex.

6. A method according to claim 1, wherein the organic polyol is a non-toxic $C_2$ to $C_{12}$ linear or branched hydrocarbon having at least 2 hydroxy groups.

7. A method according to claim 6, wherein the organic polyol is selected from the group consisting of 1,2-propanediol, 1,3-propanediol, 1,6-hexanediol, glycerol and sorbitol.

8. A method according to claim 1, wherein the organic polyol is a non-toxic $C_5$ to $C_{12}$ cyclic or heterocyclic hydrocarbon having at least 2 hydroxy groups.

9. A method according to claim 8, wherein the organic polyol is selected from the group consisting of hexahydroxy cyclohexane (inositol) and mono- and disaccharides.

10. A method according to claim 9, wherein the organic polyol is glucose, fructose or sucrose.

11. The method according to claim 1, wherein the concentration of nicotine in said aqueous suspension of a nicotine/cation exchange resin complex is from about 5% by weight to about 50% by weight.

12. The method according to claim 1, wherein the ratio of cation exchange resin to nicotine is from 1:1 to 10:1.

13. The method according to claim 12, wherein the ratio of cation exchange resin to nicotine is from 2:1 to 6:1.

14. The method according to claim 12, wherein the ratio of cation exchange resin to nicotine is about 4:1.

15. The method according to claim 1, wherein the ratio of cation exchange resin to organic polyol is from 1:1 to 10:1.

16. The method according to claim 15, wherein the ratio of cation exchange resin to organic polyol is from 2:1 to 8:1.

17. The method according to claim 15, wherein the ratio of cation exchange resin to organic polyol is about 2.4:1.

18. A method of preparing a nicotine delivery product having a nicotine release rate of at least 80% over a 10 minute period, said method comprising:
    (a) mixing an aqueous solution of nicotine with a cation exchange resin selected from the group consisting of:
        (i) a methacrylic, weakly acidic type of resin containing carboxylic functional groups,
        (ii) a polystyrene, strongly acidic type of resin containing sulfonic functional groups, and
        (iii) a polystyrene, intermediate acidic type of resin containing phosphonic functional groups;
    thereby forming a nicotine/cation exchange resin complex, (b) admixing with said complex of step (a) an organic polyol or an aqueous solution thereof to form an aqueous slurry of nicotine/cation exchange resin complex incorporating polyol; and
(c) removing water from said slurry to produce said nicotine delivery product having a nicotine release rate of at least 80% over a 10 minute period.

* * * * *